(12) United States Patent
Aufdenblatten et al.

(10) Patent No.: US 7,816,545 B2
(45) Date of Patent: Oct. 19, 2010

(54) PROCESS 054

(75) Inventors: Rhony Aufdenblatten, Visp (CH); Martin Hans Bohlin, Södertälje (SE); Laurent Ducry, Sierre (CH); Ulrika Lindblad, Södertälje (SE); Mattias Magnusson, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/270,999

(22) Filed: Nov. 14, 2008

(65) Prior Publication Data

US 2009/0182157 A1    Jul. 16, 2009

Related U.S. Application Data

(60) Provisional application No. 60/988,121, filed on Nov. 15, 2007.

(51) Int. Cl.
*C07D 317/44*    (2006.01)
(52) U.S. Cl. ...................................................... 549/437
(58) Field of Classification Search .................. 549/437
See application file for complete search history.

(56) References Cited

U.S. PATENT DOCUMENTS

| 6,156,756 | A  | 12/2000 | Hardern et al. |
| 6,251,910 | B1 | 6/2001  | Guile et al. |
| 6,525,060 | B1 | 2/2003  | Hardern et al. |
| 2003/0181469 | A1 | 9/2003 | Bohlin et al. |

FOREIGN PATENT DOCUMENTS

| WO | 9905142 | 2/1999 |
| WO | 0192263 | 12/2001 |

OTHER PUBLICATIONS

Sakai et al., Tetrahedron: Asymmetry 14 (2003) 1631-1636.*

Ranganathan et al., "2-Aza-3-Oxabicycol[2.2.1]heptene Hydrochloride: an Exceptionally Versatile Synthon for Carbocyclic Sugars and Nucleosides," Tetrahedron (1997) 53(9):3347-3362.
Jung et al., "188. Total Synthesis of Neplanocin A," Helv. Chim Acta (1983) 66:1915-1921.
Shireman et al., "Rapid syntheses of either enantiomer of important carbocyclic nucleoside precursors," Tetrahedron Lett (2000) 41:9537-9540.
Rajappan et al., "A protected form of (1S,2R,3S,4R)-4-aminocyclopentane-1,2,3-triol, a useful precursor to 5'-norcarbocyclic nucleosides," Synth Commun (2001) 31:2849.
Lee et al., "Large scale aspects of salt formation: processing of intermediates and final products," Verlag Helvetica Chimica Acta (2002) 211-217.
Springthorpe et al., "From ATP to AZD6140: the discovery of an orally active reversible P2Y12 receptor antagonist for the prevention of thrombosis," Bioorganic and Medicinal Chemistry Letters (2007) 17(21):6013-6018.
Rajappan et al., "A Protected form of (1s,2r,3s,4r)-4-Aminocyclopentane-1,2,3-Triol, a useful Precursor to 5'-nor Carbocyclic Nucleosides," Synthetic Communications (2001) 31(18):2849-2854.

* cited by examiner

*Primary Examiner*—Janet L Andres
*Assistant Examiner*—David E Gallis
(74) *Attorney, Agent, or Firm*—Pepper Hamilton LLP

(57) ABSTRACT

The present invention is directed to a process for the preparation of a diastereomerically pure dibenzoyl-L-tartrate salt of a compound of formula (III)

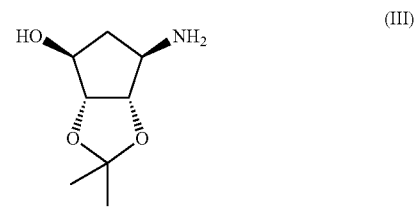

and to products of said process.

4 Claims, No Drawings

PROCESS 054

CROSS-REFERENCE TO RELATED APPLICATIONS

This application claims priority to U.S. provisional Ser. No. 60/988,121 filed Nov. 15, 2007, which is incorporated herein by reference in its entirety.

FIELD OF THE INVENTION

The present invention is directed to a process for the preparation of a diastereomerically pure dibenzoyl-L-tartrate salt of a compound of formula (III)

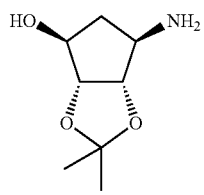

to products of said process and the use thereof.

BACKGROUND

Ranganathan, S. and George, K. S. *Tetrahedron,* 1997, 53, 3347 describes the synthesis of compound (I).

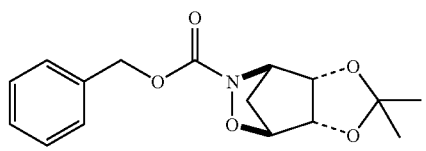

Jung, M. et al. *Helv. Chim. Acta,* 1983, 66, 1915 and Ranganathan, S. and George, K. S. *Tetrahedron,* 1997, 53, 3347 disclose the synthesis of the racemic compound (II).

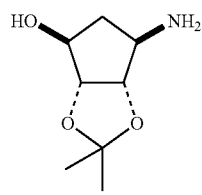

In WO99/05142, Shireman, B. T. and Miller, M. J. *Tetrahedron Lett.,* 2000, 41, 9537 and in Rajappan, V. P. et al. *Synth. Commun.* 2001, 31, 2849 the syntheses of either the free amine or the hydrochloride salt of compound (III) are described.

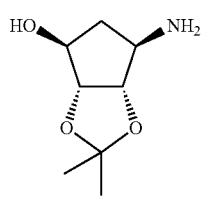

DESCRIPTION OF THE INVENTION

The present invention is directed to a process for preparing a diastereomerically pure dibenzoyl-L-tartrate salt of a compound of formula (III)

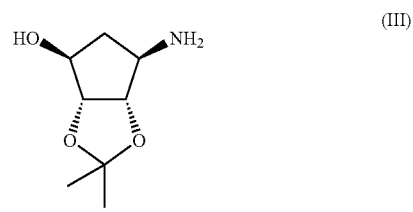

comprising the steps of
(a) mixing a compound of formula (II)

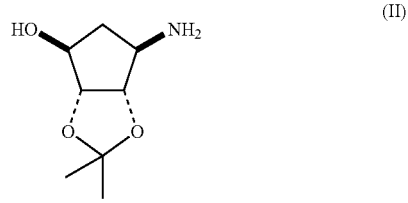

with enantiomerically pure dibenzoyl-L-tartaric acid or its monohydrate to form a diastereoisomeric salt and
(b) crystallising said salt.

The process according to the present invention is particularly useful for large-scale production of a diastereomerically pure dibenzoyl-L-tartrate salt of a compound of formula (III).

The process for preparation of a diastereomerically pure dibenzoyl-L-tartrate salt of a compound of formula (III) may start from a compound of formula (II), which may be prepared as known in the art. The compound of formula (II) is then resolved to make the desired (3aS,4R,6S,6aR)-enantiomer by crystallisation of a diastereomerically pure salt using enantiomerically pure dibenzoyl-L-tartaric acid or its monohydrate to give the corresponding diastereomerically pure dibenzoyl-L-tartrate salt of the compound of formula (III).

Alternatively, the process for preparation of a diastereomerically pure dibenzoyl-L-tartrate salt of a compound of formula (III) may start from a compound of formula (I), which may be prepared as known in the art. Compound (I) is converted to compound (II) as known in the art. Subsequently, the compound of formula (II) is resolved to make the desired (3aS,4R,6S,6aR)-enantiomer by crystallisation of a diastereomerically pure dibenzoyl-L-tartrate salt using enantiomerically pure dibenzoyl-L-tartaric acid or its monohydrate to give the corresponding diastereomerically pure salt of the compound of formula (III).

The following scheme illustrates the process for preparation of a diastereomerically pure 1:1-salt between dibenzoyl-L-tartaric acid and the compound of formula (III):

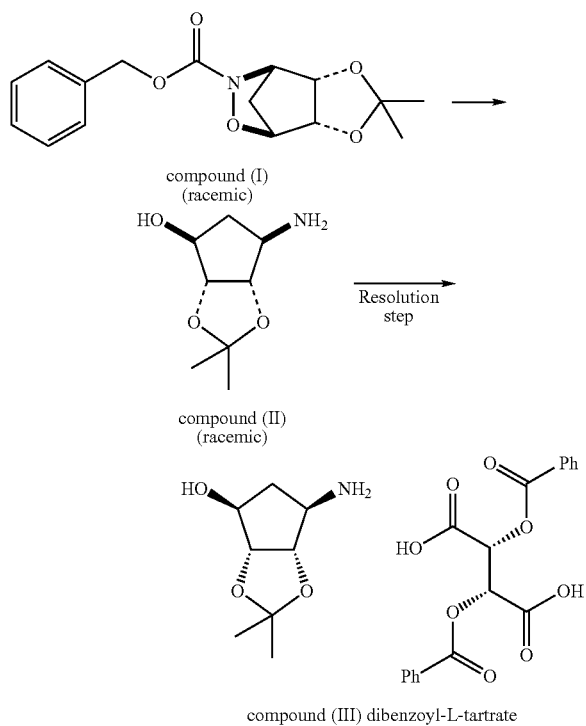

compound (I) (racemic)

compound (II) (racemic)

compound (III) dibenzoyl-L-tartrate

One embodiment of the present invention is a process for preparation of a dibenzoyl-L-tartrate of the compound of formula (III). A further embodiment of the present invention is the 1:1-salt between dibenzoyl-L-tartaric acid and the compound of formula (III). Said salt can also be named (3aR,4S, 6R,6aS)-6-amino-2,2-dimethyltetrahydro-3aH-cyclopenta [d][1,3]dioxol-4-ol (2R,3R)-2,3-bis(benzoyloxy)-3-carboxypropanoate, (3aR,4S,6R,6aS)-6-amino-2,2-dimethyltetrahydro-3aH-cyclopenta[d][1,3]dioxol-4-ol (2R, 3R)-2,3-bis(benzoyloxy)succinate or (3aR,4S,6R,6aS)-6-amino-2,2-dimethyltetrahydro-3aH-cyclopenta[d][1,3] dioxol-4-ol dibenzoyl-L-tartrate.

The enantiomerically pure acid suitable for use in the resolution step is dibenzoyl-L-tartaric acid also named (2R,3R)-2,3-bis(benzoyloxy)-3-carboxypropanoic acid or (2R,3R)-2, 3-bis(benzoyloxy)succinic acid.

Solvents useful for the resolution step giving a diastereomerically pure salt of a compound of formula (III) may be selected from aliphatic alcohols (such as methanol, ethanol, n-propanol, i-propanol, n-butanol, i-butanol and t-butanol); nitriles (such as acetonitrile); polar ethers such as tetrahydrofuran, 2-methyltetrahydrofuran, diethyleneglycol monoethers like cellosolve (ethoxyethanol), methoxyethanol, isopropoxyethanol; aliphatic esters (such as ethyl acetate, butyl acetate or isopropyl acetate); polar aprotic solvents (such as N-methylpyrrolidinone, N,N-dimethylacetamide or N,N-dimethyl-formamide); and mixtures thereof. Also, the resolution step may be performed in water or in a solution comprising water and any one of the above-listed organic solvents.

In one embodiment of the present invention, the solvent in step (a) is selected from aliphatic alcohols; nitriles; ethers; aliphatic esters; polar aprotic solvents; water and mixtures thereof.

In a further embodiment of the present invention, the solvent in step (a) is a mixture of water and an aliphatic alcohol or water and a polar ether solvent or a nitrile. In a further embodiment of the present invention, the solvent in step (a) is a mixture of water and methanol, ethanol, n-propanol, i-propanol, n-butanol, i-butanol, cellosolve (ethoxyethanol), methoxyethanol, isopropoxyethanol, tetrahydrofuran or acetonitrile.

In a further embodiment of the present invention, the solvent in step (a) is a mixture of water and ethanol.

The resolution step giving a diastereomerically pure salt of a compound of formula (III) is initially performed at temperatures from 0° C. to the boiling point of the solvent to fully dissolve the components or the formed diastereoisomeric salts. When the components have been dissolved, the temperature of the solution is adjusted to a temperature of from −50° C. to +50° C., to obtain a crystalline salt of the compound (III). The salt can thereafter be recrystallized from a solvent similar or different to the one used above to improve the optical and chemical purity.

A further embodiment of the present invention is the use of the dibenzoyl-L-tartrate of the compound of formula (III) in the preparation of {1S-[1α, 2α, 3β(1S*,2R*),5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol.

The term "diastereomerically pure salt" is defined as a salt between an enantiomerically pure cation (amine III in the present invention) and an enantiomerically pure anion (dibenzoyl-L-tartaric acid monoanion III in the present invention).

EXAMPLES

Example 1

Preparation of (3aS,4R,6S,6aR)-6-hydroxy-2,2-dimethyltetrahydro-3aH-cyclo-penta[d][1,3]dioxol-4-aminium (2R,3R)-2,3-bis(benzoyloxy)-3-carboxypropanoate (Compound (III) dibenzoyl-L-tartrate)

Procedure via isolation of compound (III):

Compound (I) (415 g, 1.36 mole) was dissolved in 1.8 L of methanol and the resulting solution was transferred to a reactor together with a slurry of Pd/C (25 g of paste containing 62% water w/w) in water (50 mL). The temperature was set to 50° C. and the reactor was flushed with nitrogen. A hydrogen pressure was applied (3 bar). The reaction was monitored by HPLC. After 3 h the reaction was complete. The methanol suspension was filtered and concentrated under reduced pressure to give 230 g (98% yield) of compound (II) as a beige-white solid that was used directly in the following step. The GC-purity for this material was >97% and the assay by titration was 95% w/w.

Compound (II) (227 g, 1.31 mole) was dissolved in 1641 g of ethanol/water-mixture (70/30 by volume) at 26° C. Dibenzoyl-L-tartaric acid monohydrate (493 g, 1.31 mole) was added allowing the inner temperature to reach 32° C. during addition. The crystallization was left for 18 hours at room temperature. The obtained crystals were filtered off and washed with 2×300 mL ethanol/water-mixture (70/30 by volume). After drying at 44° C. under vacuum for about 5 h, 272 g (39% yield or 78% of the theoretical yield) of compound (III) dibenzoyl-L-tartrate was obtained as white crystalline solid. The optical purity was 99% de (diastereomeric excess) as determined by gas chromatography on the free amine.

Example 2

Preparation of (3aS,4R,6S,6aR)-6-hydroxy-2,2-dimethyltetrahydro-3aH-cyclo-penta[d][1,3]dioxol-4-aminium (2R,3R)-2,3-bis(benzoyloxy)-3-carboxypropanoate (Compound (III) dibenzoyl-L-tartrate)

Procedure via isolation of compound (II):
Compound (II) (3.21 g, 92% purity, 17.0 mmole) was dissolved in a mixture of ethanol/water (21.6 g, 70% v/v ethanol in water) at 22° C. Dibenzoyl-L-tartaric acid (6.23 g, 17.4 mmole) was added to the clear solution. Initially, a clear solution was formed but crystallisation started after about 10 minutes. The resulting slurry was left for 2 h before the crystals were isolated by filtration and washed with an ethanol/water mixture (70% v/v ethanol in water, 2×5 mL). The crystals were dried at 40° C. under vacuum resulting in 3.31 g (37% yield) of pure compound (III) dibenzoyl-L-tartrate. The optical purity was 97.6% de as determined by gas chromatography on the free amine.

Example 3

Preparation of (3aS,4R,6S,6aR)-6-hydroxy-2,2-dimethyltetrahydro-3aH-cyclo-penta[d][1,3]dioxol-4-aminium (2R,3R)-2,3-bis(benzoyloxy)-3-carboxypropanoate (Compound (III) dibenzoyl-L-tartrate)

Procedure via isolation of compound (II):
Compound (II) (3.22 g, 92% purity, 17.1 mmole) was dissolved in a mixture of ethanol/water (21.6 g, 70% v/v ethanol in water) at 22° C. Dibenzoyl-L-tartaric acid (6.50 g, 18.1 mmole) was added to the clear solution. The resulting slurry was heated to 70° C. to dissolve the precipitate. The solution was then allowed to cool down to room temperature during 3 h before isolation of the obtained crystals by filtration. The crystals were washed with an ethanol/water mixture (70% v/v ethanol in water, 3×5 mL). The crystals were dried at 40° C. under vacuum resulting in 3.19 g (35% yield) of pure compound (III) dibenzoyl-L-tartrate. The optical purity was 98.4% de as determined by gas chromatography on the free amine.

Example 4

Preparation of (3aS,4R,6S,6aR)-6-hydroxy-2,2-dimethyltetrahydro-3aH-cyclo-penta[d][1,3]dioxol-4-aminium (2R,3R)-2,3-bis(benzoyloxy)-3-carboxypropanoate (Compound (III) dibenzoyl-L-tartrate)

Procedure via non-isolated compound (II):
Compound (I) (500 g; 1.64 mole) and Pd/C (25 g, 60% water paste) were added to a 5 L jacketed steel reactor at ambient temperature. The reactor was purged with nitrogen (3 bar). A mixture of ethanol and water (1750 g, 70/30 by volume) was added and the reactor was purged again with nitrogen (3 bar) under agitation. Hydrogen gas (3 bar) was applied and the jacket temperature was increased to 50° C. After 2 h at 50° C. no starting material could be detected and the reaction mixture was filtered to remove the Pd-catalyst. The solid catalyst was washed with ethanol/water-mixture (300 g, 70/30 by volume) and the washing liquid was combined with the rest of the solution. Dibenzoyl-L-tartaric acid (588 g, 1.64 mol.) was added to a jacketed glass vessel. The above solution of compound (II) was added at 24° C. and with slow stirring. The resulting mixture was left for about 16 h at 22° C. and the obtained crystals were then filtered off. The filter cake was washed twice with ethanol/water-mixture (2×375 mL, 70/30 by volume). The crystals were then dried until constant weight at 50° C. in a vacuum oven. This gave 324 g (37% yield, 74% of the theoretical maximum) of compound (III) dibenzoyl-L-tartrate as a white solid. The optical purity was 99.6% de as determined by gas chromatography on the free amine.

Melting point 150-151° C. (uncorrected); $^1$H NMR (400 MHz, MeOH-$d_4$) δ 7.51 (app d, J=8 Hz, 1H), 7.50 (app d, J=8 Hz, 1 H), 7.24 (app t, J=8 Hz, 2H), 4.50 (app dd, $J_1$=6 Hz, $J_2$=8 Hz, 1 H), 3.02 (app dd, $J_1$=8 Hz, $J_2$=16 Hz, 1 H), 2.86 (app dd, $J_1$=6 Hz, $J_2$=16 Hz, 1 H), 1.36 (s, 9 H); $^{13}$C NMR (100 MHz, MeOH-$d_4$) δ 171.6, 167.4, 134.5, 131.1, 131.0, 129.6, 112.4, 86.8, 84.2, 76.7, 75.0, 58.1, 35.0, 26.4, 24.0. MS [M]$^+$173; $[\alpha]_D$ (c 1.0 in methanol, 25° C.)-76.6°.

Example 5

Preparation of (3aS,4R,6S,6aR)-6-hydroxy-2,2-dimethyltetrahydro-3aH-cyclo-penta[d][1,3]dioxol-4-aminium (2R,3R)-2,3-bis(benzoyloxy)-3-carboxypropanoate (Compound (III) dibenzoyl-L-tartrate)

Procedure via non-isolated compound (II):
A solution of compound (II) (50.0 g, 0.164 mol), water (58 g) and ethanol (104 g) was treated with 5% Pd/C (1.3 g) under a hydrogen atmosphere (8 bar) at 50° C. for 18 h. The reaction mixture was cooled to 30° C., filtered, and the filter washed with a mixture of water (10.5 g) and ethanol (19.5 g). Dibenzoyl-L-tartaric acid monohydrate (61.6 g, 0.164 mol) was added. The mixture was stirred for 2 h at 28° C., cooled to 18° C. and stirred for another 2 h. Filtration, washing with a mixture of water (26.3 g) and ethanol (48.8 g) and drying afforded compound (III) dibenzoyl-L-tartrate as a white solid (31.7 g, 36% yield).

The invention claimed is:
1. A process for preparing a diastereomerically pure dibenzoyl-L-tartrate salt of a compound of formula (III)

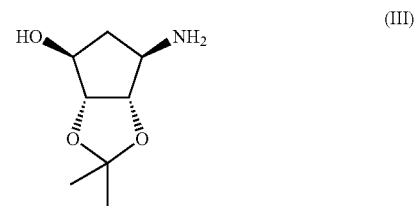

comprising:
(a) mixing a compound of formula (II)

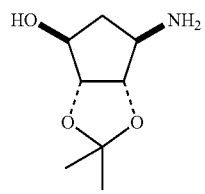

(II)

with enantiomerically pure dibenzoyl-L-tartaric acid or its monohydrate in the presence of a solvent to form a diastereoisomeric salt, wherein the solvent is a mixture of water and an aliphatic alcohol; and
(b) crystallising said salt.

2. A process according to claim 1, wherein the solvent in step (a) is a mixture of water and methanol, ethanol, n-propanol, i-propanol, n-butanol, i-butanol or t-butanol.

3. A process according to claim 2, wherein the solvent in step (a) is a mixture of water and ethanol.

4. A mono-dibenzoyl-L-tartrate salt of the compound of formula (III)

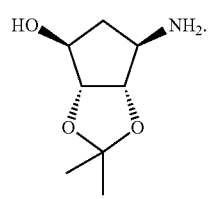

(III)

* * * * *